(12) United States Patent
Biedermann et al.

(10) Patent No.: US 12,708,421 B2
(45) Date of Patent: Aug. 18, 2026

(54) ADAPTER DEVICE FOR SURGICAL INSTRUMENTS

(71) Applicant: BIEDERMANN TECHNOLOGIES GMBH & CO. KG, Donaueschingen (DE)

(72) Inventors: Timo Biedermann, Trossingen (DE); Dimosthenis Dandanopoulos, VS-Schwenningen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 266 days.

(21) Appl. No.: 18/525,076

(22) Filed: Nov. 30, 2023

(65) Prior Publication Data

US 2024/0173060 A1 May 30, 2024

Related U.S. Application Data

(63) Continuation of application No. 17/125,403, filed on Dec. 17, 2020, now Pat. No. 11,864,806.

(Continued)

(30) Foreign Application Priority Data

Dec. 20, 2019 (EP) .................................... 19219144

(51) Int. Cl.
*A61B 17/88* (2006.01)
*A61B 17/16* (2006.01)

(Continued)

(52) U.S. Cl.
CPC ...... *A61B 17/8875* (2013.01); *A61B 17/1671* (2013.01); *G05G 1/04* (2013.01); *A61B 1/00112* (2013.01); *A61B 2017/00477* (2013.01)

(58) Field of Classification Search
CPC .................................................. A61B 17/8875
See application file for complete search history.

(56) References Cited

U.S. PATENT DOCUMENTS

| | | | |
|---|---|---|---|
| 246,382 | A | 8/1881 | Felthousen |
| 2,829,685 | A | 4/1958 | Mitchell et al. |

(Continued)

FOREIGN PATENT DOCUMENTS

| | | | |
|---|---|---|---|
| DE | 20 2007 016 245 U1 | 2/2008 | |
| EP | 2 368 514 A1 | 9/2011 | |

(Continued)

OTHER PUBLICATIONS

Extended European Search Report for Application No. 19219144.3, mailed Jun. 15, 2020, 7 pages.

*Primary Examiner* — Christian A Sevilla
(74) *Attorney, Agent, or Firm* — Womble Bond Dickinson (US) LLP

(57) ABSTRACT

An adapter device for a surgical instrument includes an adapter member connectable to and separable from the surgical instrument, the adapter member having a first end, a second end, a longitudinal axis extending from the first end to the second end, and a connection structure configured to connect to the surgical instrument, and a mounting member connectable to and separable from the adapter member for mounting an additional instrument to the adapter member.

20 Claims, 7 Drawing Sheets

Related U.S. Application Data

(60) Provisional application No. 62/951,566, filed on Dec. 20, 2019.

(51) Int. Cl.

| | |
|---|---|
| ***G05G 1/04*** | (2006.01) |
| *A61B 1/00* | (2006.01) |
| *A61B 17/00* | (2006.01) |

(56) References Cited

U.S. PATENT DOCUMENTS

| | | | | |
|---|---|---|---|---|
| 4,765,009 | A * | 8/1988 | Hung | B66F 13/00 29/245 |
| 5,211,086 | A * | 5/1993 | Shu | B25B 15/02 81/58.3 |
| 5,616,142 | A * | 4/1997 | Yuan | A61F 2/2846 606/71 |
| 5,649,931 | A * | 7/1997 | Bryant | A61B 17/8891 606/104 |
| 6,021,343 | A | 2/2000 | Foley et al. | |
| 7,166,114 | B2 | 1/2007 | Moctezuma De La Barrera et al. | |
| 7,877,890 | B2 | 2/2011 | Weber | |
| 7,967,828 | B2 | 6/2011 | Moore et al. | |
| 9,451,999 | B2 | 9/2016 | Simpson et al. | |
| 10,322,012 | B2 | 6/2019 | Palmatier et al. | |
| 11,864,806 | B2 * | 1/2024 | Biedermann | A61B 17/8875 |
| 2004/0153062 | A1 | 8/2004 | McGinley et al. | |
| 2004/0171930 | A1 * | 9/2004 | Grimm | A61B 90/39 606/80 |
| 2004/0194588 | A1 * | 10/2004 | Johnson | B25G 1/005 81/177.2 |
| 2005/0154296 | A1 | 7/2005 | Lechner et al. | |
| 2008/0140086 | A1 * | 6/2008 | Moore | A61B 17/7091 606/104 |
| 2008/0262343 | A1 | 10/2008 | Weber | |
| 2009/0145268 | A1 * | 6/2009 | Laurie | B25B 23/0028 81/177.85 |
| 2011/0034910 | A1 | 2/2011 | Ross et al. | |
| 2020/0188034 | A1 * | 6/2020 | Lequette | A61B 90/39 |

FOREIGN PATENT DOCUMENTS

| | | | |
|---|---|---|---|
| EP | 3 669 812 | A1 | 6/2020 |
| WO | WO 99/26549 | A1 | 6/1999 |
| WO | WO 2019090151 | A1 | 5/2019 |

* cited by examiner

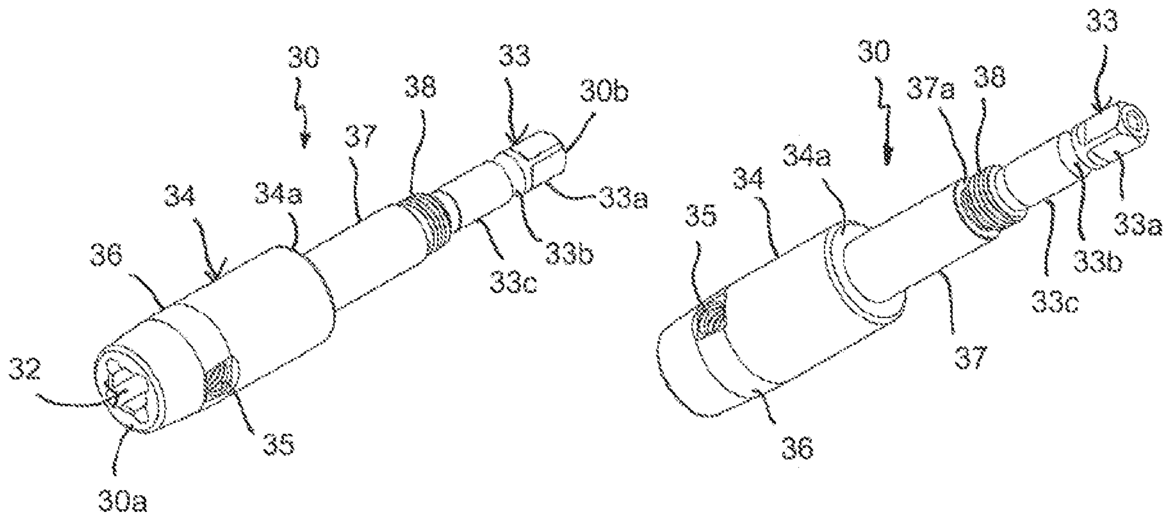
Fig.7
Fig. 8
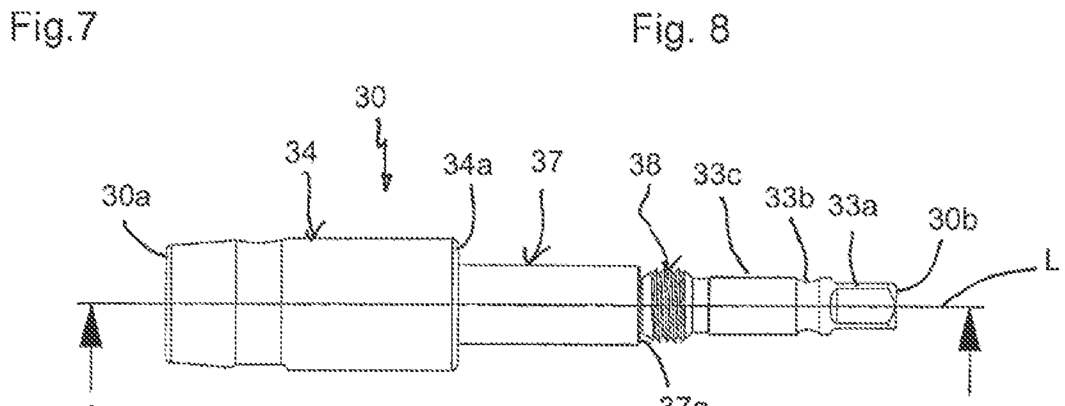
Fig. 9
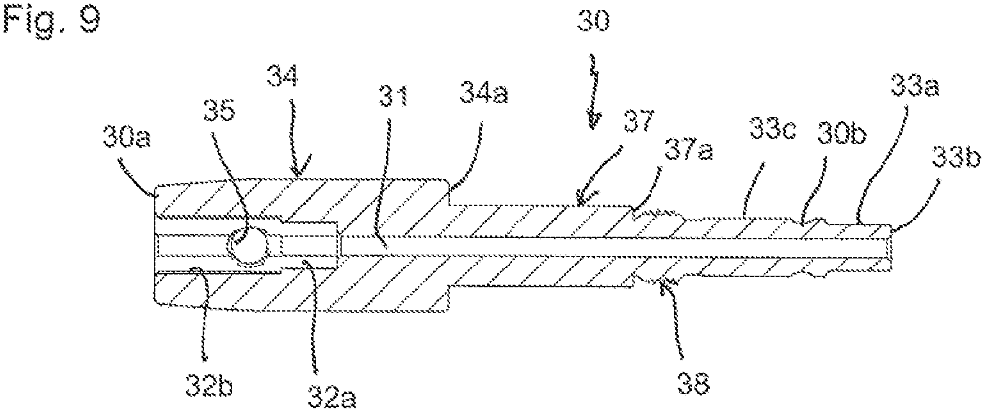
Fig.10

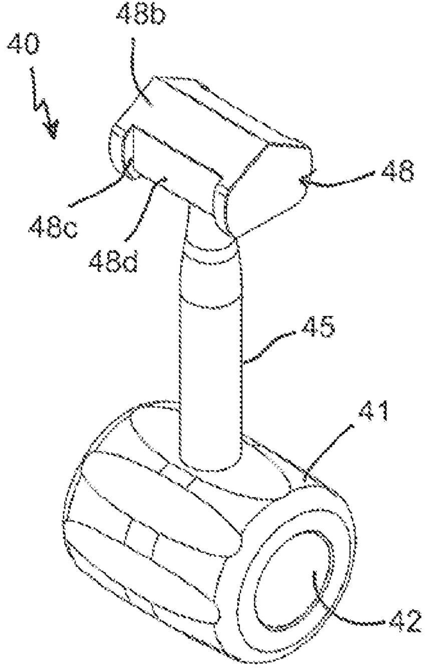
Fig. 11
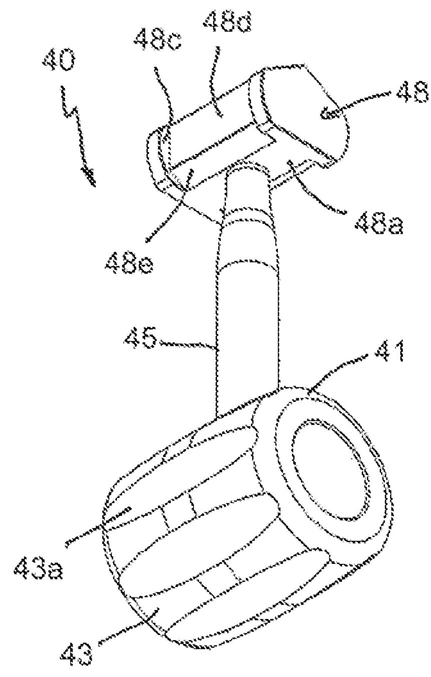
Fig. 12
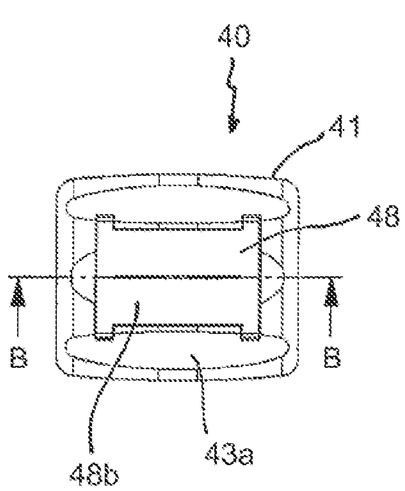
Fig. 13
48
47
40
45
44
46
41
42
Fig 14

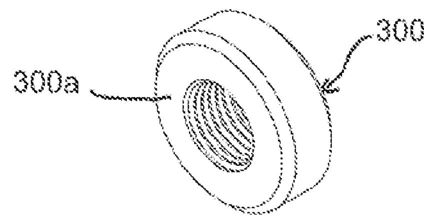
Fig. 15
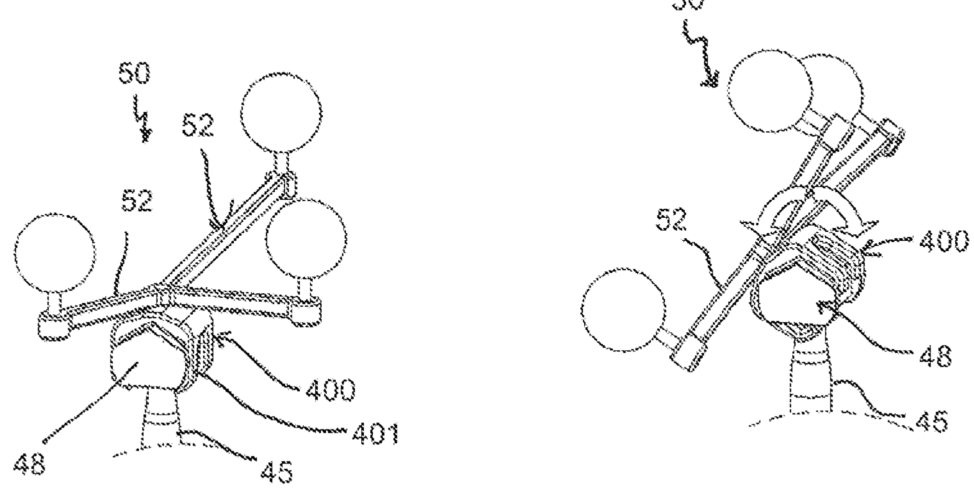
Fig. 16
Fig. 17

ADAPTER DEVICE FOR SURGICAL INSTRUMENTS

CROSS-REFERENCE TO RELATED APPLICATION(S)

This application is a continuation of U.S. patent application Ser. No. 17/125,403, filed Dec. 17, 2020, which claims priority to and the benefit of U.S. Provisional Patent Application No. 62/951,566, filed Dec. 20, 2019, the contents of which are hereby incorporated by reference in their entirety, and claims priority from European Patent Application EP 19 219 144.3, filed Dec. 20, 2019, the contents of which are hereby incorporated by reference in their entirety.

BACKGROUND

Field

The application relates to an adapter device for surgical instruments and to a system including such an adapter device and a surgical instrument. The adapter device may be employed in particular in connection with surgical instruments that have an elongate shaft.

Description of Related Art

Adapter devices that carry instrument parts used in computer guided surgery are known in the prior art. For example, US 2005/0154296 A1 describes an instrument for use in computer guided surgery that includes a shaft and a reference element adapter, wherein the reference element adapter is directly couplable to the shaft and rotatable about the shaft. A selectively operable mechanical retainer provides retention of the reference element adapter to an instrument shaft adapting interface of the instrument shaft.

U.S. Pat. No. 6,021,343 describes a trackable medical instrument for use in a computer assisted image guided medical and surgical navigation system, which includes a guide member having an emitter array for being tracked by the system and a drive shaft contained within the guide member. The drive shaft is rotatable within the guide member and fixable axially inside the guide member. A proximal end of the drive shaft has a first connector for interchangeably receiving at least one drive source, and a distal end has a second connector for interchangeably receiving at least one instrument tip.

SUMMARY

The known adapters and instruments usually are specifically adapted to each other. Thus, a variety of systems are provided by the prior art, wherein parts of one system may not normally be combined with parts of another system.

It is therefore an object of the invention to provide an improved and/or alternative adapter device for a surgical instrument and a system including such an adapter device and the surgical instrument that is easy to handle and provides for a greater variety of applications.

The adapter device for surgical instruments includes an adapter member for coupling to an end portion of a surgical instrument and a mounting member, wherein the mounting member is an exchangeable part that is configured to interchangeably connect an additional instrument to the adapter member. In particular, the mounting member is configured to interchangeably connect at least one of at least two additional instruments to the adapter member.

With the adapter device it is possible to interchangeably attach a variety of different additional instruments to a surgical instrument. Such other instruments can be instruments for navigation assisted surgery, instruments for robotic assisted surgery, simple holding devices, or many other additional instruments that are used in connection with the surgical instrument.

Moreover, the adapter device can be employed in a universal manner, as it is connectable to surgical instruments which have a standard connection portion, such as, for example, a ¼ inch coupling. Because of this, the adapter device can be used with already existing surgical instruments having such a standard connection. Hence, with the adapter device, the costs of providing a system including the adapter device and one or more surgical instruments can be reduced. Such surgical instruments may be drills, thread cutters, awls, shank inserters, shank drivers, and many others.

In addition, the adapter device can be used to easily extend or lengthen existing instruments.

As the connection between the surgical instrument and the adapter device is designed substantially free of play in the radial and/or axial directions, any surgical instrument with a shaft and/or an overall cylindrical shape can be held in position by the aid of the adapter device.

In an embodiment, the mounting member includes an arm or outrigger extending at an angle to the longitudinal axis of the adapter member, and an attachment portion provided at the arm.

In a further embodiment, the attachment portion is configured to permit mounting of the additional instrument in various positions and/or orientations. This allows in some applications for gripping of the adapter instead of the handle, to prevent the hand of the surgeon from interfering, for example, with a fluoroscopy area.

As a connection between the adapter member and the arm is substantially free of play, the instrument can be more precisely held in position, and/or a positional relationship between the surgical instrument and the additional instrument can be held or maintained very precisely.

The adapter device can be used with a surgical instrument in a manner such that the adapter device is mounted between the surgical instrument and a handle, and the surgical instrument can be held in position by gripping, for example, an arm of the mounting member with one hand while the instrument is operated via the handle with the other hand.

In one embodiment, at least two mounting members are provided, each being connected to an additional instrument, where the mounting members are exchangeably or interchangeably connectable to the adapter member.

In an embodiment, the arm is detachably mounted to the mounting member. Hence, a plurality of different arms for various functions can be attached and exchanged with one another. Also, when the arm is detachable, the arm can more easily be cleaned. In addition, the adapter device may be cannulated. This permits use of the adapter device in procedures using needles, for example.

Furthermore, a need for using a large number of specific additional instruments, for example, instruments specifically designed for working under fluoroscopy or for computer based navigation assisted surgery, can be reduced.

BRIEF DESCRIPTION OF THE DRAWINGS

Further features and advantages of the invention will become apparent from the detailed description of embodiments by means of the accompanying drawings. In the drawings:

FIG. 7 shows a perspective view from above of the adapter member of the adapter device of FIGS. 5 and 6.

FIG. 8 shows a perspective view from the bottom of the adapter member of FIG. 7.

FIG. 9 shows a side-view of the adapter member of FIGS. 7 and 8.

FIG. 10 shows a cross-sectional view of the adapter member of FIGS. 7 to 9, the cross-section being taken along line A-A in FIG. 9.

FIG. 11 shows a perspective view from a top of a mounting member of the adapter device of FIGS. 5 and 6.

FIG. 12 shows a perspective view from a bottom of the mounting member of FIG. 11.

FIG. 13 shows a top view of the mounting member of FIGS. 11 and 12.

FIG. 14 shows a cross-sectional view of the mounting member of FIGS. 11 to 13, the cross-section being taken along line B-B in FIG. 13.

FIG. 15 shows a perspective view of an axial play adjustment member of the adapter device of FIGS. 5 and 6.

FIG. 16 shows a perspective view of a portion of the arm of the adapter device of FIGS. 5 and 6, with a navigation star attached to the arm.

FIG. 17 shows a perspective view of the arm and the navigation star of FIG. 16, attached in another position.

DETAILED DESCRIPTION

Figure 1:
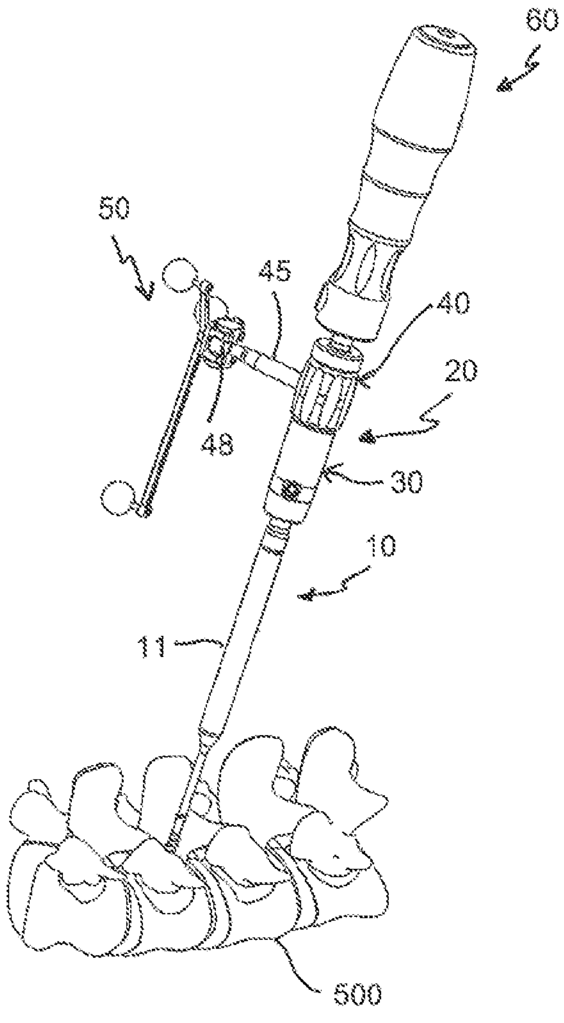
FIG. 1 shows an embodiment of a system including a surgical instrument and an embodiment of the adapter device connected to a navigation instrument when applied in spinal surgery.

FIG. 1 shows an embodiment of a system including a surgical instrument 10 and an adapter device 20 coupled thereto. The surgical instrument 10 is preferably an elongate instrument having a shaft 11 defining a longitudinal axis L, and is configured to perform a function along the longitudinal axis, such as drilling, thread cutting, screw-driving, pushing, or one or more other functions. The specific surgical instrument shown is, for example, a thread cutter for cutting a thread in a prepared hole in a vertebra 500. The adapter device 20 according to an embodiment is at one end fixedly connectable to the surgical instrument 10. At the other end, the adapter device may be fixedly connectable to a handle 60. The handle portion 60 optionally may also be part of the system. Moreover, an additional instrument 50 may be mounted to the adapter device 20 and optionally may also be part of the system. The additional instrument 50 is, for example, a navigation instrument, such as a navigation star.

Figure 2:
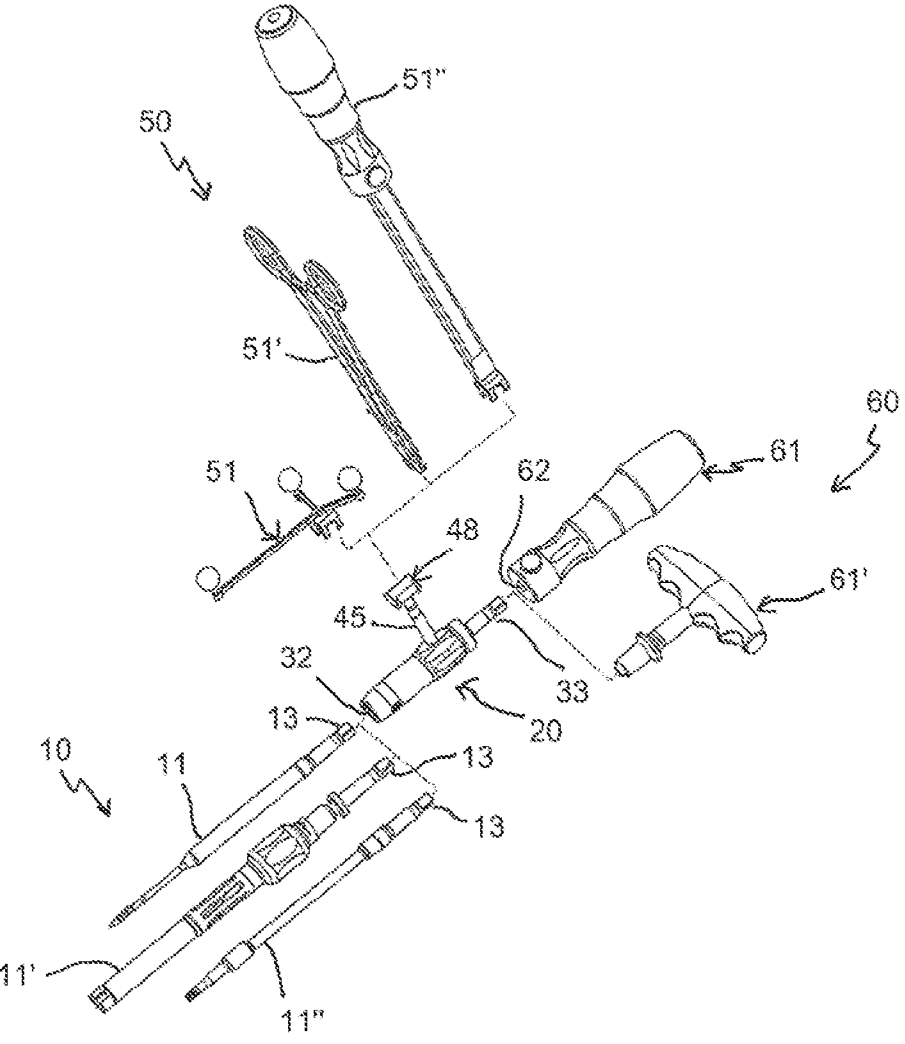
FIG. 2 shows a perspective exploded view of a system including the adapter device of FIG. 1 and various different surgical devices, various different handles, and various additional instruments attachable to the adapter device.

As shown in greater detail in FIG. 2, the surgical instrument 10 may be one of a plurality of elongate instruments with shaft. Such different shafts may be, for example, a thread cutter 11, a head placer 11', a screw-driver 11", an awl, or any other shaft-based instrument. Some additional instruments 50 may be, for example, a navigation star 51 that carries transmitters or receivers for electromagnetic radiation including light, pliers 51', a simple holder 51", a radiolucent holder, a navigation clamp, pliers, a counter-holder, and/or many other instruments. Hence, in the following, the surgical instrument 10 is also called a main instrument and the additional instrument 50 is also called a secondary instrument. The handle 60 may be one of different handle portions, such as a cylindrical handle 61, a T-handle 61', a L-handle, or any other type of handle. The handle 60 may also include a further instrument or tool such as, for example, an electric drive device. One or more main instruments and/or one or more handles and/or one or more secondary instruments together with the adapter device 20 forms a modular system. In the modular system, the main instruments 10 and the secondary instruments 50, as well as the handles 60, are each interchangeable.

Figures 3, 4:
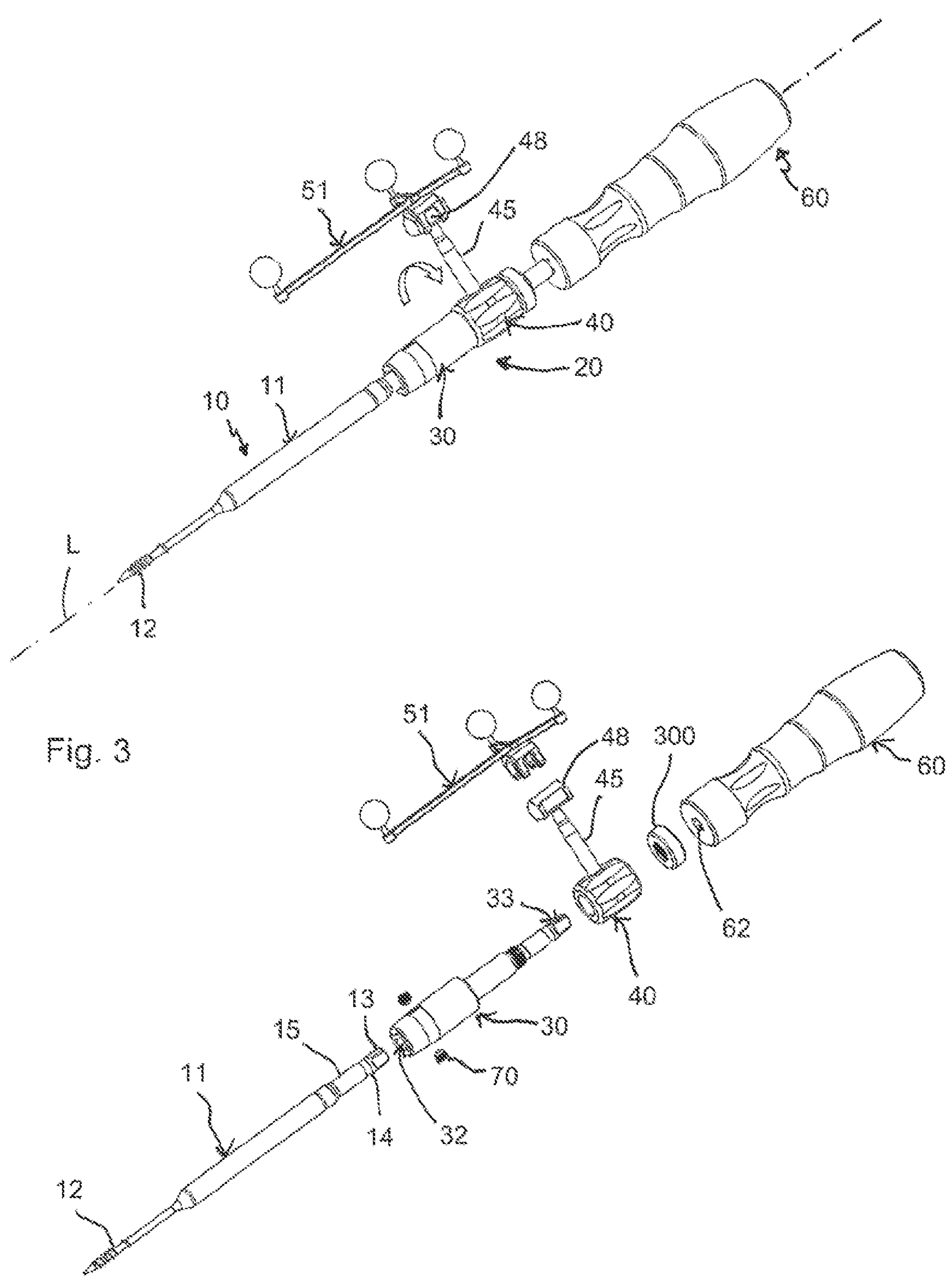
FIG. 3 shows another perspective view of the system of FIG. 1.
FIG. 4 shows a perspective exploded view of the system of FIGS. 1 and 3.
Figure 5:
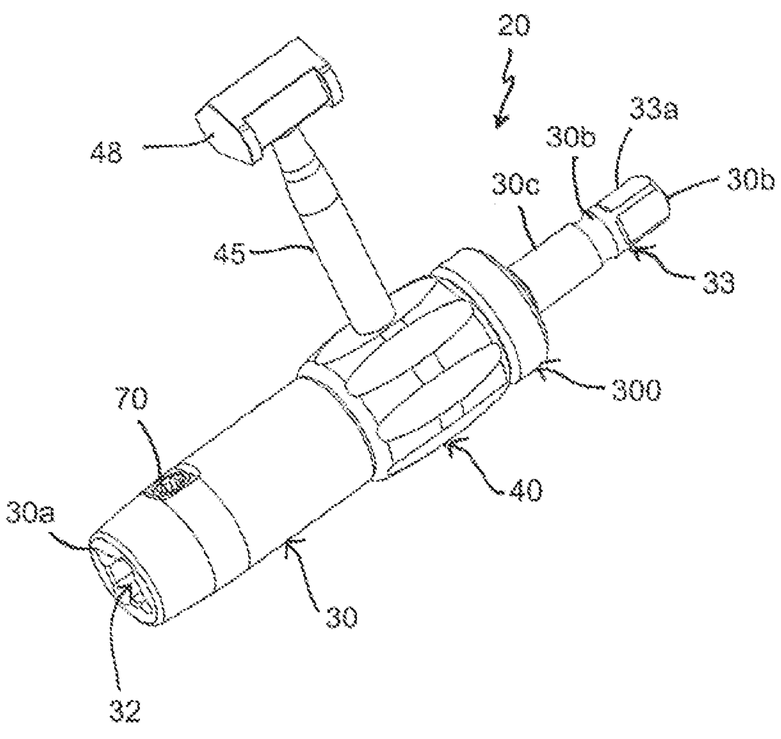
FIG. 5 shows an enlarged perspective view of the embodiment of the adapter device shown in FIGS. 1 to 4.

Referring now additionally to FIGS. 3 and 4, the surgical instrument 10 includes the shaft 11, a tip portion 12 at one end of the shaft 11, and a connection portion 13 at the opposite end of the shaft 11. The tip portion 12 is configured to perform the function of the instrument. The shaft 11 may have various shapes according to the specific instrument. The connection portion 13 in the embodiment may be designed as a male connection portion with a polygonal outer contour, such as a square-end. In a specific embodiment, the connection portion 13 may be a ¼ inch connection portion as used in many standard couplings. The shaft 11 may further include, adjacent to the connection portion 13, a cylindrical portion 15 with a small circumferential groove 14.

As shown in greater detail in FIGS. 5 to 14, the adapter device 20 includes an adapter member 30 and a mounting member 40 rotatably supported on the adapter member 30. The mounting member 40 may be connected to the secondary instrument 50.

The adapter member 30 is a substantially elongate part with a first end **30*a* and an opposite second end 30*b*, and a longitudinal axis L extending through the first end 30*a* and the second end 30*b*. When the adapter member 30 is mounted to the surgical instrument 10, the longitudinal axes L of the adapter member 30 and of the surgical instrument 10 are coincident or coaxial. A channel 31 which is coaxial with the longitudinal axis L may extend through the adapter member 30 from the first end to the second end. Hence, the adapter member 30 may be cannulated. In a region at the first end 30*a*, a first connection structure 32 is formed that is configured to cooperate with the mating connection portion at the surgical instrument 10. In greater detail, the first connection structure 32 includes a female socket connection portion 32*a* configured to cooperate with the male connection portion 13 of the surgical instrument 10. For example, the female socket connection portion 32*a* may be shaped as a polygonal recess, such as a square-recess, for example, as the female part of a ¼ inch connection. The first connection structure 32 may also have a guiding portion 32*b* that extends between the end surface of the first end 30*a* and the female connection portion 32*a*. The size of the female socket portion 32*a* is such that the male connection portion 13 of the instrument can be received therein, substantially free of play. The guiding portion 32*b* is configured to accommodate at least a part of the cylindrical portion 15 of the shaft 11 which includes the groove 14. A cross-section of the guiding portion 32***b* may also be polygonal, for example, square-shaped with a slightly greater width and longitudinal grooves in the corners.

In the region of the second end, a second connection structure 33 is provided that is configured to cooperate with a mating connection structure 62 at the handle 60. In the embodiment, the second connection structure 33 is shaped identically to the connection structure of the instrument, including a male connection portion 33*a*, such as a polygonal structure, and more particularly a square-end such as a ¼ inch male connection portion. The male connection portion 33*a* is followed by a cylindrical portion 33*c* in which a circumferential groove 33*b* is formed. The mating connection structure 62 at the handle is identical to the first connection structure 32 of the adapter member.

The first connection structure 32 is provided in a first portion 34 of the adapter member adjacent to the first end 30*a*. The first portion 34 of the adapter member 30 may have a substantially cylindrical outer shape that may slightly taper and narrow towards the first end 30*a*. The first connection structure 32 is arranged in a coaxial manner therein and extends to a distance away from the first end 30*a* that is sufficient to receive the connection structure of the instrument 10 to a sufficient length.

Two opposite transverse threaded holes 35 may be formed at a distance from the first end 30*a* in the first portion 34, and may extend through the wall of the first portion 34 into the guiding portion 32*b*. The axial position of the threaded holes 35 corresponds to the position of the groove 14 of the connection portion of the main instrument 10 when the connection portion 13 is received in the connection structure 32 of the adapter member 30. The threaded holes are configured to receive threaded pins 70 therein. The threaded pins 70 have a rounded, preferably a spherical, front end 70*a* that is configured to press into the groove 14 of the mating connection structure at the surgical instrument 10. Thereby, the connection portion of the instrument can be centered within the adapter member and firmly clamped therein. A length of the pins 70 is such that when the pins 70 are screwed into the threaded holes 35, the rear end of the pins 70 does not protrude out of the adapter member 30. For achieving this, a circumferential groove 36 may be provided in the outer surface of the first portion 34 at the axial position of the threaded holes 35. The circumferential groove 36 has an axial width such that the threaded holes 35 are located therein.

Adjacent to the first portion 34, there is a second portion 37 which has a cylindrical outer diameter and forms a support for the mounting member 40. The second portion 37 has a smaller diameter than the first portion 34, thereby forming a shoulder 34*a* between the portions. A length of the second portion 37 in the axial direction is such that it corresponds substantially to an axial length of the mounting member 40. Between the second portion 37 and the cylindrical portion 33*c* of the second connection structure 33, a third portion 38 with an external thread may be provided that receives an adjustment member 300 which will be explained in greater detail below. The third portion 38 slightly tapers and narrows towards the second portion 37, so that a step 37*a* is formed between the second portion 37 and the third portion 38. Moreover, an outer diameter of the third portion 38 may be slightly smaller than an outer diameter of the second portion 37.

Referring now in greater detail to FIGS. 3 to 6 and 11 to 14, the mounting member 40 will be described.

The mounting member 40 is a separate part from the adapter member 30 and is configured to be detachably connectable to the adapter member.

Figure 6:
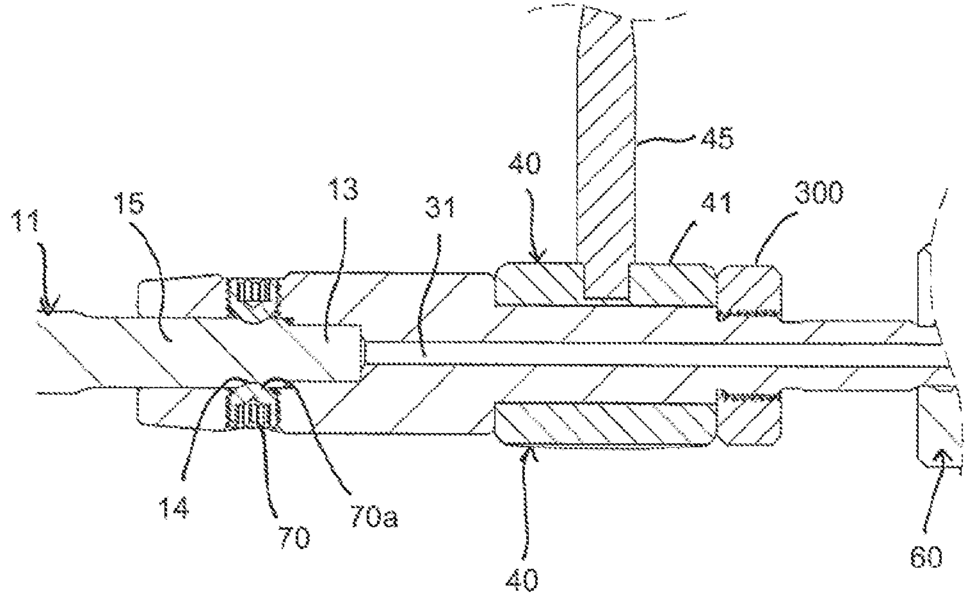
FIG. 6 shows a cross-sectional view of the adapter device of FIG. 5, the cross-section being taken in a plane including a longitudinal axis of an adapter member and a longitudinal axis of an arm of the adapter device.

The mounting member 40 includes a sleeve-shaped part 41 with a cylindrical inner surface 42 that has an inner diameter which may only be slightly greater than an outer diameter of the second portion 37 of the adapter member 30, such that the sleeve-shaped part 41 can be mounted onto the second portion 37 and rotate thereon. In particular, the mounting member can rotate smoothly, i.e., in a stepless manner 360° around the adapter member. A length of the sleeve-shaped part in the axial direction corresponds to a length of the second portion 37. Hence, when the mounting member 40 is mounted onto the adapter member 30, and more specifically onto the second portion 37 of the adapter member 30, one end of the sleeve-shaped part 41 is confined by or abuts against the step 37*a*, while the other end is substantially flush with the corresponding end of the second portion 37, as shown in FIG. 6. An outer surface of the sleeve-shaped part 41 may be substantially cylindrical. Longitudinal flat portions or shallow grooves 43*a* may be formed in the outer surface that extend substantially parallel with one another and are arranged substantially equidistantly in the circumferential direction. Furthermore, in the outer surface 43 of the sleeve-shaped part 41, a mounting portion 44, such as a mounting recess, is formed that facilitates attachment of an arm 45 to the sleeve-shaped part 41. The mounting recess may be cylindrical and sized so as to receive a mating first connection portion 46 provided at one end of the arm 45. The connection between the first attachment portion 46 and the mounting recess 44 may be, for example, a press-fit connection. The arm 45 may be detachably mounted to the sleeve-shaped part 41 or may be permanently mounted thereto. In an alternative embodiment, the arm 45 may be formed monolithically with the sleeve-shaped part 41.

The arm 45 may be substantially cylindrical, and the connection between the mounting portion and the first connection portion 46 may be such that the longitudinal axis of the arm 45 is substantially perpendicular to the sleeve axis of sleeve-shaped part 41 of the mounting member 40. Hence, when the arm 45 is mounted to the sleeve-shaped part 41, the arm 45 extends radially from the longitudinal axis L of the adapter member 30. At the end opposite to the first connection portion 46, the arm 45 includes a second connection portion 47 that is configured to connect to an attachment member or attachment portion 48 for attaching a secondary instrument 50. An outer diameter of the arm 45 may taper and narrow towards the second connection portion 47. The second connection portion 47 may be, for example, a cylindrical end portion with a smaller diameter than the rest of the arm 45, which fits into a mounting recess 49 at a lower side of the attachment member 48.

The attachment member 48 may have a shape that resembles a prism with a base 48*a* that includes the second mounting recess 49, a roof 48*b* opposite to the base 48*a*, and rounded edges between the base 48*a* and the roof 48*b*. Recesses 48*c* may be formed on opposite long sides of the attachment portion 48 between the base 48*a* and the roof 48*b*, which may be arranged to sequentially provide vertical and angled surfaces 48*d*, 48*e* between the roof 48*b* and the base 48*a*. Hence, the roof 48*b*, together with the vertical surface 48*d*, the angled surface 48*e*, and the base 48*a* provide a clamping surface in the form of an irregular polygon that allows for adjusting of a clamping member mounted thereon to various different positions. The attachment member 48 may be detachable from the arm 45 or may be fixedly connected to the arm 45. In an alternative embodiment, the attachment member 48 is monolithically formed with the arm 45.

Several mounting members with different additional instruments connected thereto can be provided and used interchangeably. Such mounting members can differ in shape.

It shall be noted that the additional instrument can also be fixed to the mounting member and can even be formed monolithically with the mounting member, for example, the additional instrument can be monolithically formed with the arm.

Referring in particular to FIGS. 6 and 15, the adjustment member 300 is formed as a nut member that is configured to be screwed onto the threaded third portion 38 of the adapter member 30. An axial length of the adjustment member 300 is such that it extends substantially along the third portion 38 and abuts with its front face 300*a* against the step 37*a*. An outer diameter of the adjustment member 300 may be the same or smaller than an outer diameter of the sleeve-shaped portion 41 of the mounting member 40. The adjustment member 300 is configured to adjust and confine the axial length of the region in which the mounting member can rotate, and is more specifically configured to adjust the axial play of the mounting member relative to the adapter member. In a case in which different mounting members can be connected selectively to the adapter member, the adjustment member is able to adjust the axial play for each of the mounting members, for example, if the respective axial lengths of the different mounting members are different.

The adapter device 20 may be preassembled with the mounting member 40 mounted onto the second portion 37 of the adapter member 30. When the adjustment member 300 is screwed onto the third portion 38 until its front end 300*a* abuts against the step 37*a*, the mounting member 40, or more specifically the sleeve-shaped part 41, is mounted to the adapter member 30 substantially free of play. Simultaneously, the mounting member 40 is rotatably supported on the adapter member 30. Hence, a rotation of the adapter member 30 relative to the mounting member 40 maintains an exact position between the arm 45 and the longitudinal axis L of the adapter member 30. As a result, any secondary instrument 50 mounted to the attachment member 48 can be maintained at a constant axial positional relationship relative to the adapter member 30.

In use, the adapter device 20 with the mounting member 40 including the arm 45 and the attachment member 48 is coupled to the connection portion 13 of a main instrument via the first connection structure 32 of the adapter member. The connection between the main instrument 10 and the adapter member 30 can be centered, and in addition made substantially free of play, by screwing the pins 70 into the threaded holes 35 until they press into the groove 14 of the main instrument 10. By means of this, an orientation of the secondary instrument 50 relative to the main instrument 10 is precise and does not change during actuating of the main instrument. The second connection portion 33 of the adapter member may be coupled to the mating connection portion 61 of a handle 60. A secondary instrument may be attached to the attachment member 48.

An example for attaching a secondary instrument in the form of the navigation star 51 is shown in FIGS. 16 and 17. As shown in FIG. 16, the navigation star 51 may be connected via a clamp 400 onto the attachment portion 48. The clamp 400 has substantially mating inner surfaces that are configured to cooperate with the surfaces formed by the recess 48*c* of the attachment portion 48. Flexible arms 401 of the clamp 400 may snap around the roof 48*b* and the vertical side surfaces 48*d* within the recess 48*c*. Hence, with the manner of attachment shown in FIG. 16, arms 52 of the navigation star 51 can be oriented substantially perpendicular to the axis of the arm 45. In FIG. 17, an inclined attachment of the navigation star 51 is shown. In this case, the clamp 400 engages the attachment portion 48 in a configuration where the arms 52 of the navigation star 51 extend at an angle to the axis of the arm 45, and therefore also at an angle to the longitudinal axis L of the adapter device 20. As shown by the arrows in FIG. 17, various angled positions of the navigation star 51 can be selected by rotating the clamp 400.

Depending of the field of application, one method of use can include actuating the main instrument 10 through the handle 60 with one hand, for example rotating the handle, wherein the rotational movement of the handle is transmitted via the adapter member 30 to the main instrument. Simultaneously, the secondary instrument 50 can be kept stationary by gripping it with the other hand. Thereby, the orientation of the secondary instrument to the tip portion 12 of the main instrument is substantially maintained. In the case of navigation assisted surgery, for example, when the secondary instrument is a navigation star, the navigation star maintains its position relative to the navigation system. In another method of use, the handle can be omitted.

Various other modifications of the embodiments described are also conceivable. The parts are not limited to their detailed shape as depicted in the embodiments. In particular, the shapes of the adapter member and the mounting member are not limited to the specific shapes shown. The adapter member does not need to be cannulated. The arrangement of male/female connection portions is also not limited to the arrangement shown, but can be interchanged. The arm can also be mounted such that it extends at an angle different than 90° relative to the longitudinal axis of the adapter member. The instruments are also not limited to the specific instruments shown in the figures or mentioned as examples.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An adapter device for a non-implantable surgical instrument, the adapter device comprising:

an adapter member connectable to and separable from the surgical instrument, the adapter member having a first end, a second end, and a longitudinal axis extending from the first end to the second end, and comprising a first connection structure at the first end configured to connect directly to the surgical instrument in a direction of the longitudinal axis and a second connection structure at the second end; and a mounting member connectable to the adapter member in an unlatched and rotatable manner and separable from the adapter member, wherein the mounting member comprises an engagement surface configured to mount an additional instrument to the adapter member;

wherein the mounting member defines a cylindrical recess extending therethrough to receive the adapter member and is devoid of any other projections or recesses that are configured to engage with another portion of the adapter device to hold a relative position of the mounting member to the adapter member.

2. The adapter device of claim 1, wherein the engagement surface of the mounting member is formed on an attachment portion for interchangeably attaching a plurality of additional instruments.

3. The adapter device of claim 2, wherein the engagement surface comprises at least two outer surfaces angled relative to one another to facilitate adjustment of an orientation of one of the plurality of additional instruments that is attached thereto.

4. The adapter device of claim 1, wherein the mounting member further comprises an arm that extends transversely to the longitudinal axis of the adapter member.

5. The adapter device of claim 4, wherein the arm is separable from other portions of the mounting member.

6. The adapter device of claim 1, further comprising an adjustment member configured to hold the mounting member to the adapter member and to adjust an axial play of the mounting member relative to the adapter member.

7. A system comprising:

the adapter device of claim 1; and the surgical instrument comprising an end portion with a corresponding connection structure configured to cooperate with the first connection structure of the adapter member.

8. The system of claim 7, wherein the adapter member is connectable to the surgical instrument substantially free of play.

9. The adapter device of claim 1, wherein the mounting member is rotatable around the longitudinal axis in a stepless manner relative to the adapter member.

10. The adapter device of claim 1, wherein the mounting member is formed as a sleeve configured to surround at least a portion of the adapter member.

11. The adapter device of claim 1, wherein no portion of the mounting member is surrounded radially by any portion of the adapter member.

12. The adapter device of claim 1, wherein the adapter member is a monolithic part, the mounting member is a monolithic part, and the adapter member and the mounting member are configured to directly engage one another.

13. A system comprising:

a non-implantable surgical instrument configured to facilitate implantation of an implant into a patient;

an adapter device comprising an adapter member connectable to and separable from the surgical instrument, the adapter member having a first end, a second end, and a longitudinal axis extending from the first end to the second end, and comprising a first connection structure at the first end configured to connect directly to the surgical instrument in a direction of the longitudinal axis and a second connection structure at the second end, and a mounting member connectable to and separable from the adapter member, wherein the mounting member comprises an engagement surface configured to mount an additional instrument to a lateral side of the adapter member; and a holder releasably attachable to the engagement surface of the mounting member and to extend laterally away from the longitudinal axis of the adapter device.

14. The system of claim 13, wherein the adapter member is connectable to the surgical instrument substantially free of play.

15. The system of claim 13, wherein the surgical instrument comprises a head placer configured to engage and hold a head of an anchoring element therein to facilitate anchoring of the anchoring element to a bone of a patient.

16. The system of claim 13, further comprising a navigation instrument releasably attachable to the engagement surface of the mounting member, wherein the holder and the navigation instrument are interchangeably connectable to the mounting member.

17. A system comprising:

a non-implantable surgical instrument configured to facilitate implantation of an implant into a patient;

an adapter member connectable to and separable from the surgical instrument, the adapter member having a first end, a second end, and a longitudinal axis extending from the first end to the second end, and comprising a first connection structure at the first end configured to connect directly to the surgical instrument in a direction of the longitudinal axis and a second connection structure at the second end;

a first mounting member connectable to and separable from the adapter member, wherein the first mounting member comprises an engagement surface configured to mount an additional instrument to a lateral side of the adapter member, and defines a recess extending therethrough to receive the adapter member, and wherein a body of the first mounting member defining the recess has a first axial length;

a second mounting member connectable to and separable from the adapter member, wherein the second mounting member defines a recess extending therethrough to receive the adapter member, and wherein a body of the second mounting member defining the recess has an axial length that is different from the first axial length; and an adjustment member connectable to the adapter member in a manner such that the first and second mounting members are configured to be interchangeably connectable to and held to the adapter member by the adjustment member.

18. The system of claim 17, wherein a held axial position of the adjustment member is adjustable relative to the adapter member to accommodate the different axial lengths of the first and second mounting members.

19. The system of claim 17, wherein a held axial position of the adjustment member is adjustable relative to the adapter member to adjust an axial play of the first or second mounting member relative to the adapter member.

20. The system of claim 17, wherein at least one of the first or second mounting members is configured to connect a navigation instrument to the adapter member.

* * * * *